United States Patent [19]
Byerly et al.

[11] Patent Number: 5,228,398
[45] Date of Patent: Jul. 20, 1993

[54] KILN CONTROL FOR INCINERATING WASTE

[75] Inventors: Harold L. Byerly, Houston; Bruno R. Kuhn, Nassau Bay; Donald C. Matter, Houston, all of Tex.; Eustathios Vassiliou, Newark, Del.

[73] Assignee: Rollins Environmental Services, Inc., Wilmington, Del.

[21] Appl. No.: 908,056

[22] Filed: Jul. 6, 1992

[51] Int. Cl.$^5$ .............................................. F23G 5/00
[52] U.S. Cl. .................................. 110/246; 110/185; 110/186; 110/259; 110/346; 110/165 R
[58] Field of Search ............... 110/246, 226, 346, 259, 110/185, 186, 165 R; 432/103; 73/861.32, 861.35

[56] References Cited
U.S. PATENT DOCUMENTS

4,846,083  7/1989  Serbent ........................ 110/246 X
5,081,940  1/1992  Motomura et al. ................ 110/346

Primary Examiner—Edward G. Favors
Attorney, Agent, or Firm—E. Vassiliou

[57] ABSTRACT

A method and apparatus for controlling the viscosity of slag contained in a rotary incinerating kiln by detecting the position at which the slag exits the outlet of the kiln, thereby determining changes in the viscosity of the slag. If the viscosity deviates from a predetermined range of values, appropriate additives are supplied to the slag for bringing the viscosity back to within the range of the predetermined values. There is also disclosed a method and apparatus for measuring viscosity as "angular" viscosity.

30 Claims, 4 Drawing Sheets

KILN CONTROL FOR INCINERATING WASTE

FIELD OF THE INVENTION

This invention relates to methods and devices for controlling rotary incinerating kilns for waste materials. More particularly it pertains to methods and devices for controlling the slag which is formed in such rotary incinerating kilns. This invention also relates to methods of measuring viscosity in general.

BACKGROUND OF THE INVENTION

Incinerator rotary kilns have an outside metallic shell, usually steel, the inside of which is fully covered by a thick ceramic wall, usually in the form of fire bricks having a total thickness exceeding in many cases 25 cm. These kilns operate at a temperature in the range of about 1,800° to 2,200° F. The ceramic walls, however, are very vulnerable to erosion and corrosion, due to the hostile conditions created by the nature of incinerated materials and high temperatures, especially, if alkali metals are present. If the viscosity of slag in the kiln is adequately high, it may form a rather thick viscous coating on the ceramic and thus protect it from the hostile environment. However, when the viscosity of the slag is very low, the slag contributes to the erosion and corrosion of the ceramic, both chemically because it serves as a solvent and mechanically, as it allows foreign big pieces of abrasive material to act against the ceramic walls. If the slag is viscous to the point of becoming substantially solid, or if it has never been formed as liquid, it becomes ineffective in promoting combustion of organic matter, and also in capturing toxic heavy metals. Therefore, it is imperative that the viscosity of the slag is very carefully monitored and controlled within a range of values. Thus, one of the objects of this invention is to detect and correct the viscosity of the slag in rotary incinerating kilns. In addition, this invention provides a novel method of measuring viscosity of liquids in general.

SUMMARY OF THE INVENTION

As aforementioned, this invention relates to methods and devices for controlling rotary incinerating kilns for waste materials. More particularly it pertains to an incinerating kiln device capable of controlling the viscosity of molten slag contained within and discharged from the kiln, the device comprising a rotary kiln having a substantially cylindrical shape, an outside skin, a center axis, an inlet, and an outlet opposite the inlet, the kiln being inclined so that the slag exits from the outlet at a discharge position, and wherein the center axis and a line crossing the center axis and having the direction of gravity define a plane of zero position, the distance between the discharge position and the plane of zero position being an indirect measure of the angular viscosity of the slag, as defined hereinbelow, the higher said distance the higher the angular viscosity;

first detection means at the outlet of the kiln for detecting the distance between the discharge position and the plane of zero position, thus determining the angular viscosity of the slag; and means for correcting the viscosity of the slag, if the distance between the plane of zero position and the discharge position deviates from a desired value, by feeding an additive to the inlet of the kiln.

This invention also pertains to a method for controlling the viscosity of a molten slag in an incinerating rotary kiln comprising the steps of:

a) feeding waste into an inlet of the kiln, the kiln being inclined and having a substantially cylindrical shape, a skin, a center axis, and an outlet opposite the inlet, so that the slag exits from the outlet at a discharge position, and wherein the center axis and a line crossing the center axis and having the direction of gravity define a plane of zero position, the distance between the discharge position and the plane of zero position being an indirect measure of the angular viscosity of the slag, the higher said distance the higher the angular viscosity;

b) detecting the distance between the discharge position and the plane of zero position, thus determining the angular viscosity of the slag; and c) correcting the viscosity of the slag, if the distance between the plane of zero position and the discharge position deviates from a desired value, by feeding an additive to the inlet of the kiln.

The kiln device may further comprise computer means for processing data received from the distance detection means and thereby control the viscosity correcting means.

The distance detecting means or first detection means may comprise a series of heat-resistant rods positioned in a direction substantially parallel to the center axis of the kiln under the outlet of the kiln in a manner that discharged slag falls on at least one of the rods producing a mechanical perturbation on the rod, so that depending on which rod(s) the perturbation occurs, the distance between the discharge position and the plane of zero position is determined. The perturbation may be detected by a strain gauge mounted at a position of the rod at which the operability of the gauge is not substantially affected by the effects of the kiln and the falling slag. The perturbation may also be detected by electromechanical means.

In the device and method described above, the distance detecting means may comprise optical means. In one embodiment, the optical means may comprise a series of photocells positioned under the outlet of the kiln and having a direction of detecting mode substantially parallel to the center axis of the kiln so that depending on which photocell detects falling slag, the distance between the discharge position and the plane of zero position is determined. In another embodiment, the optical means may comprise infra-red means, and still in a different embodiment, the infra-red means may comprise an infra-red scanner. Preferably, the infra-red means are positioned under the outlet of the kiln and have a direction of scanning mode substantially perpendicular to the center axis of the kiln so that depending on the position of the scan when falling slag is detected, the distance between the discharge position and the plane of zero position, as well as the slag temperature, may be determined.

The viscosity correcting means may comprise bins for containing additives and feeding additives to the kiln.

The kiln device may comprise second detection means for detecting and monitoring the temperature of the slag at the outlet of the kiln. It may also comprise third detection means for detecting and monitoring the temperature of the skin of the kiln. In addition, it may comprise means for lowering the temperature of the slag through the skin of the kiln, by using fans for example.

The present invention also pertains more generally to a method of determining the angular viscosity of a liquid, as defined hereinbelow, comprising the steps of:
a) feeding the liquid at a predetermined rate to an inlet of a hollow, inclined, rotating, substantially cylindrical body, the cylindrical body having a center axis, and an outlet opposite the inlet,
   so that the liquid exits from the outlet at a discharge position, and
   wherein the center axis and a line crossing the center axis and having the direction of gravity define a plane of zero position,
   the distance between the discharge position and the plane of zero position being an indirect measure of the angular viscosity, the higher said distance the higher the angular viscosity; and
b) detecting the distance between the discharge position and the plane of zero position, thus determining the angular viscosity of the liquid.

Furthermore, this invention pertains to an apparatus for determining the angular viscosity of a liquid comprising:
a) a hollow, inclined, substantially cylindrical body, the cylindrical body having a center axis, an inlet, and an outlet opposite the inlet;
b) means for rotating the cylindrical body;
c) means for feeding the liquid at a predetermined rate to the inlet of the cylindrical body;
   so that the liquid exits from the outlet at a discharge position, and
   wherein the center axis and a line crossing the center axis and having the direction of gravity define a plane of zero position,
   the distance between the discharge position and the plane of zero position being an indirect measure of the angular viscosity, the higher said distance the higher the angular viscosity; and
d) means at the outlet of the cylindrical body for detecting the distance between the discharge position and the plane of zero position, thus determining the angular viscosity of the liquid.

The absolute viscosity of liquids at high temperatures is very difficult to detect and measure by conventional techniques. However, many times a change in viscosity is much more important than the absolute value of the viscosity. As briefed above, and described in detail later, this invention pertains to a new technique for detecting and measuring such changes. The technique is capable of measuring absolute viscosity if the appropriate mathematical calculations are carried out, and or correlation measurements are performed with respect to other better studied and well established techniques. The present method and apparatus introduce a new term, "angular viscosity", as they are based on passing a liquid through a rotating hollow cylindrical body, such as a kiln for example, and measure the distance between a discharge position and a plane of zero position, as explained later. This distance is an indirect measure of the viscosity, under a certain set of parameters and conditions, the higher this distance the higher the viscosity. As this distance increases from zero to higher values, the more it approaches the value of the radius of the cylindrical body the larger the change in viscosity has to be for the same change in distance. A change in distance, therefore, indicates a change in viscosity, but the value of the change also depends on the initial and final values of the discharge position.

This effect may be minimized by defining the "angular viscosity" as the angle which has a sine equal to the ratio of the "distance between the discharge position and a plane of zero position" to the "radius or half the diameter of the cylindrical body".

BRIEF DESCRIPTION OF THE DRAWING

The reader's understanding of practical implementation of preferred embodiments of this invention will be enhanced by reference to the following description taken in conjunction with the drawing figures, wherein

FIG. 2b illustrates schematically the side view of the embodiment of FIG. 2a.

DETAILED DESCRIPTION OF THE INVENTION

As previously mentioned, this invention relates to methods and devices for controlling rotary incinerating kilns for waste materials. More particularly, it pertains to methods and devices for controlling the angular viscosity of slag contained in a rotary incinerating kiln by detecting the position at which the slag exits the outlet of the kiln, thereby determining the angular viscosity of the slag, as defined above and explained in more details hereinbelow. If the viscosity deviates from a predetermined range of values, appropriate additives are supplied to the slag for bringing the viscosity back to within the range of the predetermined values. It also pertains to combinations of other important parameters which are vital for the efficient operation of rotary incineration kilns, as discussed in detail hereinwith.

Figure 1:
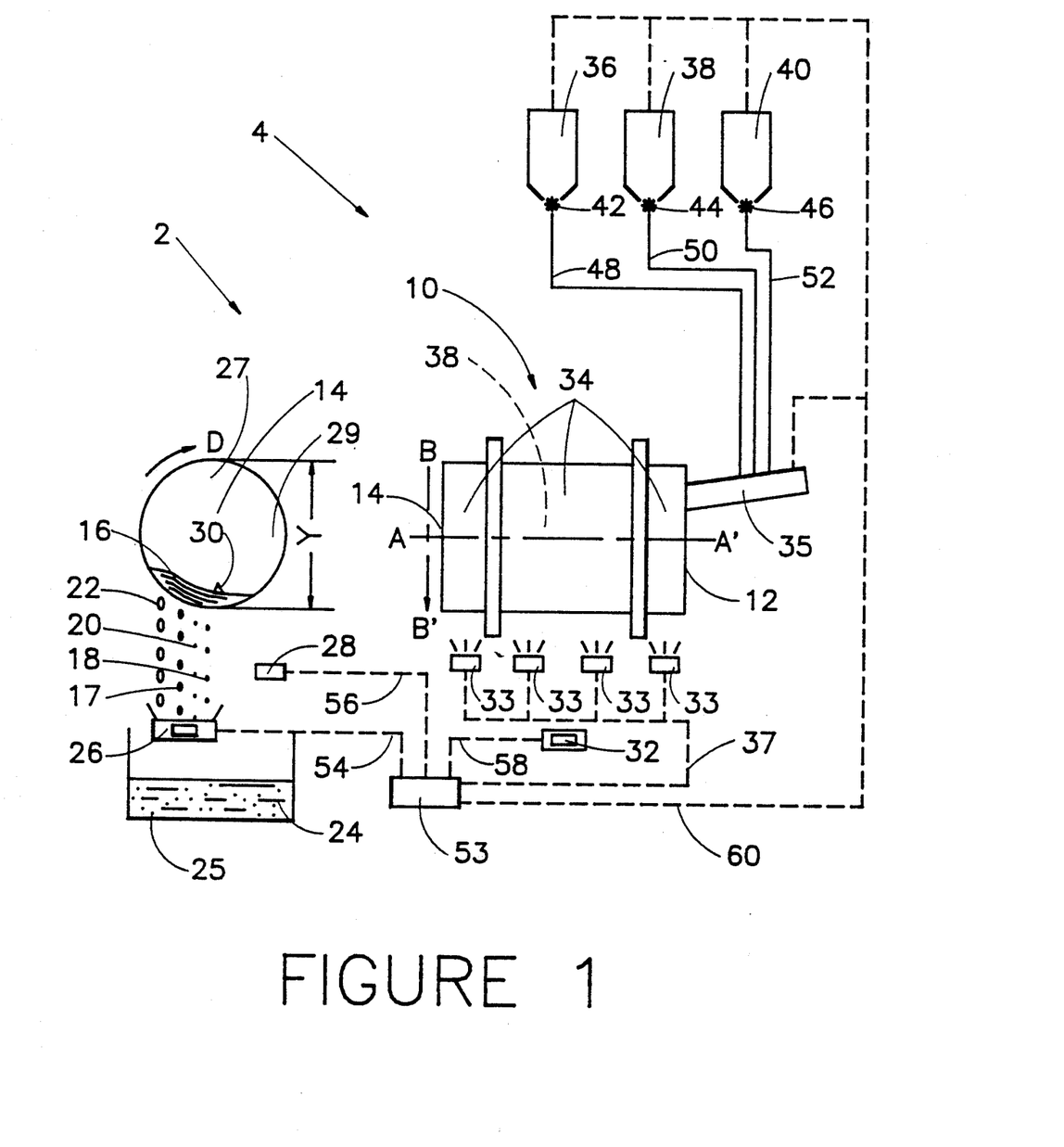
FIG. 1 shows schematically a combination of the front view and the side view of a kiln device according to one embodiment of the present invention.

Referring now to FIG. 1 there is depicted the front view 2 and the side view 4 of a rotary kiln 10, according to a preferred embodiment of this invention. The kiln 10 has an inlet 12 for waste material feeding, and by outlet 14, which is an exit for the off-gases (not shown) and slag 16. The slag 16 is produced by the waste, as well as by different additives fed usually through the inlet of the kiln. The slag may be newly formed in its totality, or it may be recirculated, depending on the desired performance of the kiln. Liquid or gaseous waste materials may be fed through lances (not shown) or other mechanisms, well known to the art of kilns. For purposes of clarity, fuel burners and other conventional devices needed for the operation of the kiln are not shown, since they are well known to the art of incinerating kilns.

The rotary kiln 10 has a substantially cylindrical shape. It also has a diameter Q, a center axis A—A', an inlet 12, and an outlet 14 opposite the inlet 12. The kiln is inclined, preferably 1-8 degrees, more preferably 2-6 degrees, and even more preferably 3-4 degrees. During operation, the kiln also rotates in a predetermined direction D, preferably at 0.05 to 0.5 rpm, and more preferably at 0.1 to 0.25 rpm, when the diameter Q of the kiln is 3–5 meters. The combination of the inclination and the rotation forces the slag 16 to exit from the outlet 14 at a discharge position 17. If the viscosity of the slag is very low, the discharge position 17 will be in the vicinity of the center or zero position 18. If the viscosity is higher, then the discharge position 17 will be in the vicinity of an intermediate position 20, while if the slag has an even higher viscosity, the discharge position 17 will be in the vicinity of a far position 22.

The center axis A—A' and a line B—B' crossing the center axis and having the direction of gravity define a plane of zero position. The center or zero position 18 lies on the same plane. The distance between the discharge position 17 and the plane of zero position is an indirect measure of the angular viscosity of the slag; the higher the distance the higher the angular viscosity. This is because as the viscosity of the slag increases, the slag tends to climb higher on the inside walls (not shown) and at the outlet 14 of the kiln. This in turn results in forcing the slag to drop at a distance away from the plane of zero position. Thus, the distance between the discharge position 17 and the plane of zero position is an indirect measure of the viscosity of the slag. If the slag has low viscosity, and as a result it falls in the vicinity of the zero position, it has the form of small droplets or even a continuous stream. As the viscosity increases, the slag starts dripping in larger and larger chunks.

It is preferable that regardless of the discharge position, slag 16 falls into a tank of water or deslagger 24. The deslagger 24 may have a continuous belt (not shown) at its bottom end 25 for removing the slag. The deslagger 24 serves the purpose of cooling the slag fast and breaking it into smaller and more manageable pieces.

Between the bottom of outlet 14 and the watertank or deslagger 24, there is disposed a first detection means 26 for determining the position at which slag 16 drops or discharge position 17. The viscosity of slag 16 may thus be judged from the distance of the discharge position and the plane of zero position, which plane is defined by the center axis A—A' and line B—B', as already discussed. The first detection means may include any type of device, such as mechanical, electromechanical, optical, sonic such as "Sonar" for example, other radiation, and the like.

Figure 2A:
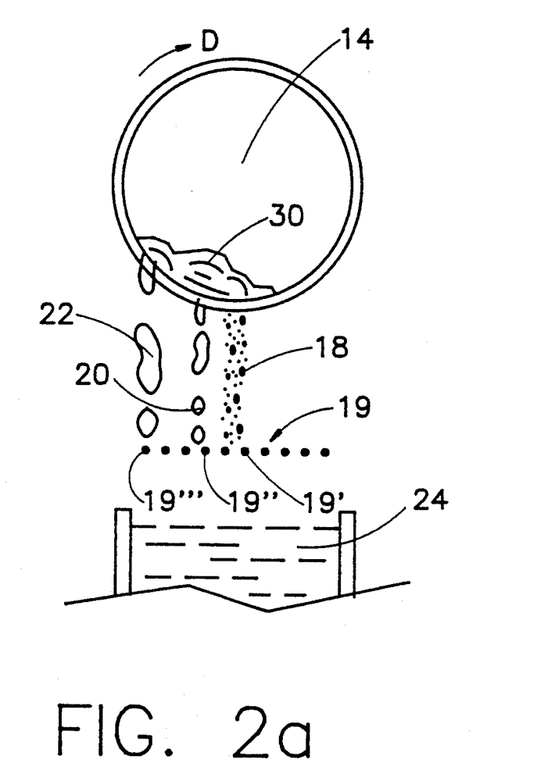
FIG. 2a illustrates schematically the front view of the kiln with a series of rods for detecting the position of discharge of the slag in one embodiment of this invention.
Figure 2B:
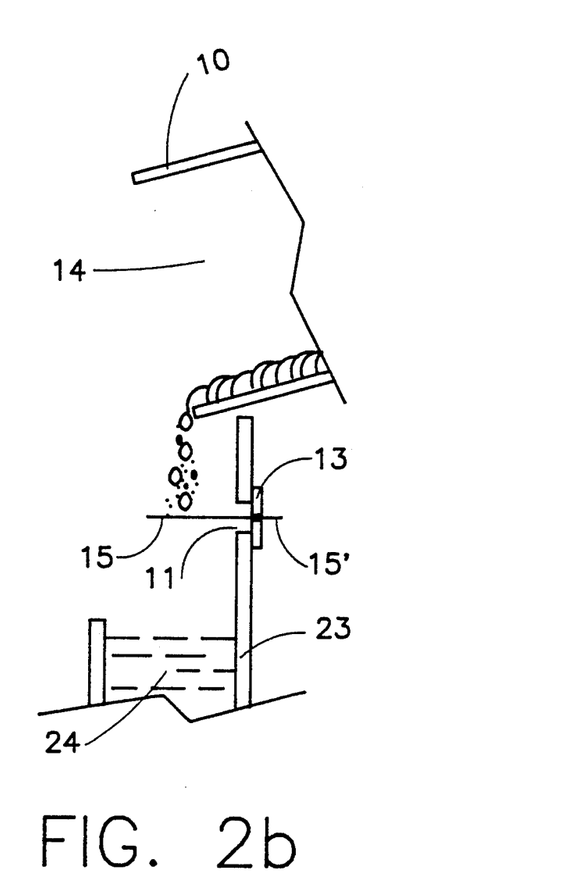

An example of a mechanical device is a series of rods 19 in the region of positions 18, 20 and 22, as better shown in FIG. 2a and FIG. 2b. Depending on where the discharge position is, the slag will fall in the vicinity of rod 19' or rod 19'' or rod 19''', thus producing a perturbation on the respective rod. Each rod has an inside portion 15 and an outside portion 15'. The rods are supported in position by a coupling 13 and extend through hole 11 of wall 23 of the deslagger 24. The coupling 13 may be of resilient material, preferably heat resistant in nature, such as for example silicone rubber. As long as the coupling material allows the perturbations occurring on the inside part 15 of the rods 19, to be transferred to the outside part of the rod 15', the material is suitable for the purposes of this invention, as long as it can withstand the conditions encountered by the wall 23. The detection of the perturbation may be performed by a strain gauge, preferably mounted on the outside portion 15' of the rods 19, using conventional techniques, well known to the art. The perturbations may also be detected by using a ferromagnetic material in portion 15', and placing a coil around the ferromagnetic material. Vibrations on the ferromagnetic material will produce accordingly varying inductive resistance to an electric potential applied at the leads of the coil. Also, if at least part of the outside portion 15' is a magnet with a coil around it, the magnet will produce a varying electric potential at the leads of the coil upon vibration of the magnet which will correspond to the vibrations of the outside part 15' transferred from the perturbations of the inside part 15. Vibration switches or detectors may also be used at the outside portion 15' to detect perturbations occurred on the inside portion 15 of the rods 19. One example is that of Series 440 switches of PMC/BETA Limited Partnership, 4 Tech Circle, Natick, Mass. 01760. These solid state switches are mainly used for detecting vibrations in rotating machinery. They have adjustable time delay, a limit for alarm, a limit for shutdown, as well as a limit for vibration severity. An analog output of 4–20 mA may also be provided for remote readout, computer interface, and the like. These and other conventional means may be used to detect the perturbations under consideration. The outside portion of the rod 15' is such that the operability of gauges, or other mechanisms mounted on it are substantially not affected by the effects of the kiln (temperature, corrosive environment, and the like) and the falling slag.

The thickness of the rods is preferably in the range of 0.5 to 1.5 cm. Stainless steel is the preferable construction material for the rods, especially with a coating of graphite around each rod to provide non-stick properties and discourage the falling slag from building up on the rods. When one of the rods 19 becomes inoperable for some reason, it may be preferably pushed through hole 11 and disposed of in the deslagger so that it may be replaced by a new rod.

Figure 3:
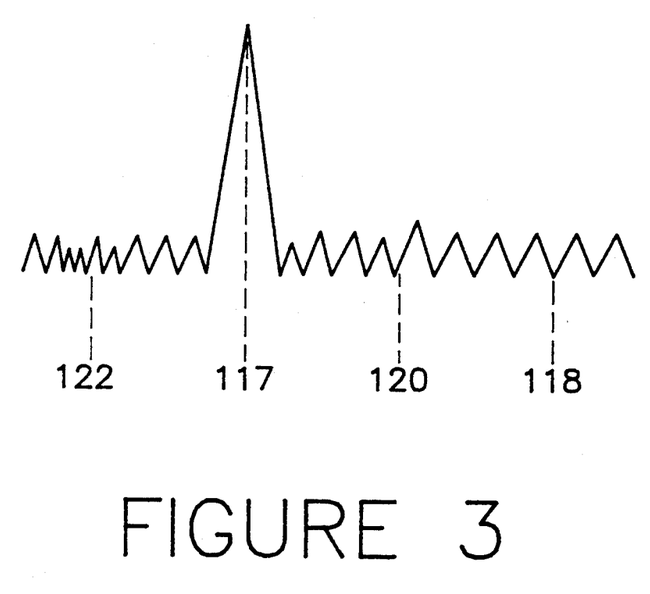
FIG. 3 represents the shape of a signal corresponding to the detection of the position at which the slag falls according to one embodiment of the present invention.

Instead of using detection means of mechanical and/or electromechanical nature, one may use other detection means, such as for example optical means. One example of an optical device for this purpose is a series of electrooptic cells replacing the rods illustrated in FIGS. 2a and 2b. Instead of the perturbations on the rods, the electrooptic cells or photocells may have substantially linear optical paths which will be interrupted by the dripping slag, or will be activated by the light produced by the dripping slag. A different example of optical means is a scanner, such as for example an infrared scanner, preferably with a memory and segmented integrator, which may give a signal as shown for example in FIG. 3, where 117 represents the discharge position of the slag as compared to the center or zero position 118, intermediate position 120 and far position 122. Of course, lasers, radar, x-ray and other radiation devices may also be utilized in a similar manner.

In a different embodiment of this invention, in an appropriate position for optical communication, there is disposed a second detection means 28 for measuring the temperature of slag 16, preferably at a center point 30. This may preferably be an infrared device suitable for measuring temperatures. This temperature device may be part of the scanner discussed above. Of course other devices, like thermocouples, etc. may also be utilized, and then optical communication is not required.

An example of an infra-red scanner, which may perform both functions described above is "Thermoprofile® 5", made by AGEMA, Infra-Red Systems, 550

County Avenue, Secaucus, N.J. This instrument can scan the outlet of the rotary kiln in a plane under the kiln edge and indicate both temperature and location. Additionally, the screen on the host computer can be sectionalized into zones, each zone having its own alarm limits. This allows an output to a control computer to take proper action which includes adding additives, increasing temperatures, and lowering temperatures.

In another embodiment of this invention, there is also provided a third detection means 32 for monitoring the temperature of the skin 34 of the kiln 10, preferably in a continuous manner. An infrared scanner as the one described above may be used in this case also.

In still another embodiment of this invention, there is provided a plurality of fans 33 for cooling the skin 34 of the kiln 10.

In still a different embodiment of this invention, there is disposed in the vicinity of the Inlet 12, a particulate injector 35 which is used to inject additive particulate matter to the inside portion 38 of the kiln 10. The additive particulate matter is useful in controlling the viscosity of the slag 16, and to improve the binding of any heavy metals into the slag. The additive particulate matter is stored in a number of bins, such as for example, bins 36, 38 and 40, which have feeding valves 42, 44 and 46, respectively, and they communicate with injector 35 through feeding lines 48, 50 and 52, respectively. The additive in bin 36 may be a viscosity builder, such as silica for example, while the additive in bin 38 may be a viscosity reducer, such as glass for example. Bin 40, as well as other bins (not shown) may contain other additives, such as slag for recirculation, for example.

Data collected in detectors 26, 28 and 32 are fed to computer 53 through input line 54, 56 and 58 respectively. The data, after being processed in computer 53, are used to control bins 36, 38, 40, injector 35 through output multiple line 60, the fans 33 through line 37, as well as other functions of the kiln 10 (output lines not shown), such as for example feeding of waste material, burner (not shown), etc.

In operation, kiln 10 is rotated while burning waste material, and the viscosity of the slag 16 is arranged so that the position of discharge 17 is within an upper and a lower limit. The upper limit may be set to be the far position 22, for example, and the lower limit may be set to be the intermediate position 20, for example, depending on the desired latitude of viscosity range that is acceptable in a particular occasion. The first detection means 26 detects that slag falls within the acceptable range, and sends a signal to computer 53 in that effect. Computer 53 is programmed cause all valves (42, 44 and 46) to be closed, and injector 35 to be inactivated.

If, for some reason, the slag discharge position moves between positions 18 and 22, the computer 53, having received the respective signal from first detection means 26, causes the valve 42 for example to open and provide the injector 35 with a slag-thickener, sand for example, contained in bin 36. In sequence, injector 35 is ordered by computer 53, and throws into the kiln 10 the sand received from bin 36 preferably throughout the majority of the kiln length for faster reaction with the slag 16. After a predetermined delay, and depending on whether the slag discharge position has moved the acceptable range or not, the computer may cause more slag viscosity thickener to be injected, or it may relax.

On the other hand, If for some reason, the slag discharge position moves over position 22, the computer 53, having received the respective signal from first detection means 26, causes the valve 44 for example to open and provide the injector 35 with a slag viscosity reducer, glass for example, contained in bin 38. In sequence, injector 35 is ordered by computer 53, and throws into the kiln 10 the glass received from bin 36 preferably throughout the majority of the kiln length for faster reaction with the slag 16. After a predetermined delay, and depending on whether the slag discharge position has moved the acceptable range or not, the computer may cause more slag viscosity reducer to be injected, or it may relax.

Depending on the additive contained in the rest of the bins, such as bin 40, for example, the additive, powdered slag for recirculation for example, may be added in a similar manner. If the recirculating slag has very high viscosity, it may be used as a viscosity builder or thickener. On the other hand if the recirculating slag has very low viscosity, it may be used as a viscosity reducer.

Thus, depending on the degree of deviation from the acceptable range, a stronger or weaker viscosity modifier (thickener or reducer) or a combination thereof may be activated by the computer, through valves 42, 44, and 46.

The above process is continued to ensure that the viscosity of the slag does not fall under the predetermined value of intermediate position 20, or over the predetermined value of far position 22. Adequate delays have to be built in the computerized system so that no overshooting occurs, and therefore feeding of sand and glass is only used to correct viscosity deviations caused by the waste and not by the one or the other or both.

In certain occasions, the viscosity of the slag 16 may become so high, that small amounts of slag may start climbing to the top 27 or even the opposite side 29 of the kiln, and dripping therefrom. This usually does not present a problem because it may easily be recognized, and taken into account by the first detection means and the computer. First, the slag in these occasions drips in considerably larger lumps, and the frequency of dripping is highly reduced. In addition, due to the inclination of the kiln, the slag falling from the top 27 drips in a displaced position with regard to the slag falling from the bottom of the outlet 14 of the kiln 10.

An additional detector similar to the first detection means, having a scanning mode perpendicular the scanning mode of the first detection means may be used to detect the displaced positions, if any, and cause appropriate corrections. Of course, the first detection means may detect any slag discharge position towards the opposite side 29, without the need of any corrective measures.

Although the amount of slag in the kiln has some bearing on the discharge position, this amount usually is controlled within narrow limits, and thus it does not change substantially the results.

The above actions are taken, of course, after ensuring that the slag and gas temperatures of the kiln are within specified limits.

The second detection means 28 measures the temperature of the slag 16 at a central point 30 and feeds the information to computer 53, which in turn orders corrective actions if the temperature of the slag for example is too high or too low, by for example lowering the waste burning rate, turning fans 33 on or off or controlling their speed for cooling or not cooling the skin 34 of the kiln, lowering the fuel feed to the fuel burner (not shown), and the like.

The third detection means can monitor the skin temperature of the kiln, and by feeding information to the computer 53, may indirectly control also the fans 33 mentioned above, as well as activate alarms or other preventing or corrective devices.

A combination of the data of all detectors in the computer give information which may be used for corrective action, depending on each particular case. For example, by using well known to the art relationships, the refractory thickness may be estimated from the slag temperature, the skin temperature, the ambient temperature, the gas velocity, the refractory thickness, and the refractory heat conductivity. This information may be used in turn to take corrective action, and also translated to expected refractory life. Abnormally cold spots, for example, are indicative of large accumulations of slag or waste. These build-ups may be melted down or burned-up by adjusting the length of the flame of the fuel burner, or by using additional burners. On the other hand, abnormally hot spots are indicative of low-viscosity slag, high internal temperature, thickness decrease of the refractory, and the like. Corrective action should also be taken in this case. If for example the internal or gas temperature is too high, the burner should be adjusted accordingly to lower the temperature. If the viscosity of the slag is too low specified gas and slag temperature conditions, an additive, such as sand for example, should be added to raise the viscosity. Turning one or more of the fans on or to a higher speed has also a beneficial effect, especially because the portion of the slag towards the refractory cools down, and as the viscosity increases, the corrosive action of the slag against the refractory is reduced considerably.

Figure 4:
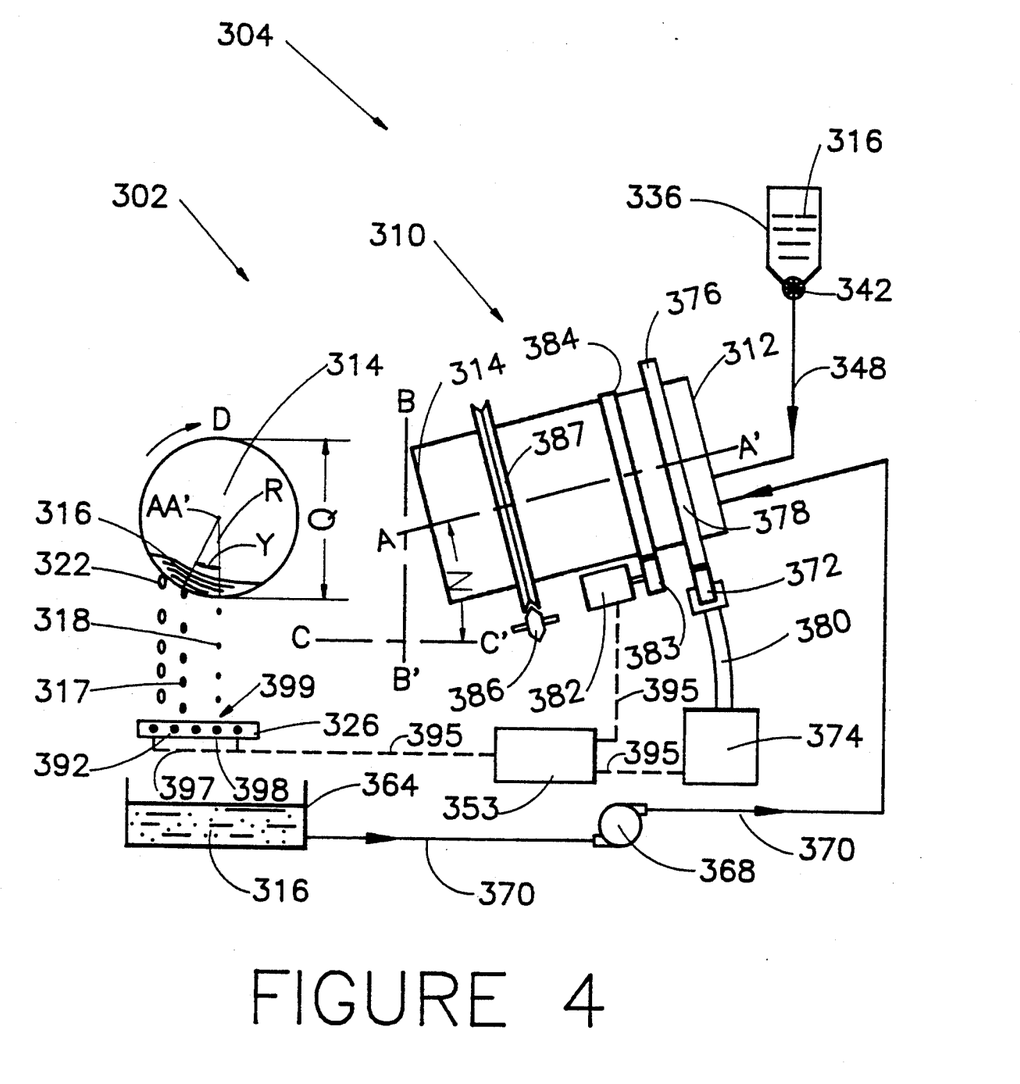
FIG. 4 shows schematically a combination of the front view and the side view of an apparatus for measuring the angular viscosity of liquids according to one embodiment of the present invention.

In a more general sense, this invention also pertains to an apparatus for determining the angular viscosity of liquids. A schematic representation is illustrated in FIG. 4. In FIG. 4 there is depicted the front view 302 and the side view 304 of a hollow substantially cylindrical body 310, according to a preferred embodiment of this invention. The cylindrical body 310 has an inlet 312 for a liquid 316 to be fed in, and an outlet 314, which is an exit for the liquid. The cylindrical body 310 has also a length, which is defined as the distance between the inlet 312 and the outlet 314, a diameter Q and a radius R. The liquid 316, as it exits the cylindrical body 310, falls into a tank 364. A pump 368 may force the liquid 316 back to the inlet 312 of the cylindrical body 310 through a recirculation line 370 at any predetermined rate. Alternatively, the liquid 316 may be provided by bin 336, through valve 342 and feed line 348. Regardless of the feeding mechanism at the inlet 312, the liquid exits from the outlet 314 at a discharge position 317, while the cylindrical body rotates, as explained below.

The cylindrical body has a center axis A—A' and an inclination with respect to a horizontal line C—C', which horizontal line is on the same plane defined by the axis A—A' and a line B—B' having the direction of gravity and crossing axis A—A'. The plane which is defined by the axis A—A' and the line B—B' is called the plane of zero position, for reasons explained hereinunder. The axis A—A' and the horizontal line C—C' form an angle of inclination Z. This angle of inclination is variable and it may be changed by raising or lowering a first idle support wheel 372 acting on a first ring 376 and controlled by a conventional height adjuster 374 through arm 380. Preferably more than one, and more preferably two support wheels 372 (only one shown for purposes of clarity) all being connected to arm 380 are used to support or nest the cylindrical body 310 at the lower part 378 of the first ring 376.

The inside surface (not shown) of the cylindrical body 310 should be preferably polished for reproducibility purposes. Examples of preferable suitable materials for construction of the cylindrical body, and especially its inside portion, are inert materials, such as for example stainless steel, glass, quartz and the like.

The cylindrical body 310 may be used at room temperature or it may be heated. If the cylindrical body 310 is heated, the tank 364, line 370 and liquid 316, are also preferably heated for maintaining a desired temperature more easily and accurately. Heating of the different portions of the apparatus are used when the behavior of the liquid with regard to viscosity is to be studied at temperatures different than room temperature. These portions may also be cooled for similar purposes.

A motor 382 is capable of causing the cylindrical body to rotate in a direction D through active wheel 383, which acts on a second ring 384.

Two (only one shown for purposes of clarity) second idle support wheels 386, acting on a third ring 387 and located near the outlet 314, are used to support and allow the cylindrical body 310 to be rotated freely around its center axis C—C'.

Between the outlet 314 and the tank 364, there is located detection means 326 for detecting the discharge position 317 and its distance from the plane of zero position, thus determining the angular viscosity of the liquid. As already explained in other embodiments of this invention, this distance is an indirect measure of the angular viscosity, the larger this distance the higher the angular viscosity, if all other parameters are kept constant. As already defined, the angular viscosity is represented by angle Y, the sine of which equals the ratio of the distance of the discharge position from the plane of zero position to the radius R.

The first detection means 326 may include any type of device, such as mechanical, electromechanical, optical, sonic, other radiation, and the like. In this embodiment, optical means are preferred. One example of an optical device for this purpose is a series of electrooptic cells, which may have substantially linear optical paths. These paths may be interrupted by the exiting liquid, and thus the discharge position 317 may be determined. Electrooptic cells and their operation are very well known to the art.

There is also provided a computer 353 for receiving and processing data form the first detection means 326, the motor 382, the height adjuster 374, through input lines 395, as well as from other sections of the apparatus (input lines not shown). The computer may also be used to order different sections of the apparatus to perform desired tasks depending of the received and processed data, by techniques well known to the art. The different active components of the apparatus may be controlled and adjusted by the computer, or manually, depending on the degree of automation desired in the operation of the apparatus.

Preferable ranges of the operational parameters of the apparatus for smoother and more reliable operation are:
(a) Length in the range of 5 to 30 cm; the more viscous the material the shorter the preferable length;
(b) Diameter in the range of 3 to 15 cm; the more viscous the material the larger the preferable diameter;

(c) Rotational linear speed in the range of 0.1 to 20 cm per second; the more viscous the material the smaller the preferable rotational linear speed;

(d) Inclination angle in the range of 5 to 45 degrees; the more viscous the material the larger the preferable inclination; and (e) Feeding rate in the range of 0.1 to 10 cc per second; the more viscous the material the higher the preferable feeding rate, as long as not excessive accumulation occurs.

Of course, it should be understood that the above ranges are only preferable ranges and should not be construed as limiting the breadth of the invention. Any other ranges and combinations suitable for a particular liquid are considered as lying within the realm of this invention.

In operation of this embodiment, the cylindrical body 310 is positioned by the height adjuster 374 to attain a predetermined inclination angle Z. Valve 342 of bin 336 is opened adequately to allow liquid 316 to enter the input 312 of the cylindrical body 310 at a predetermined rate. The system is allowed to equilibrate so that the rate of liquid 316 exiting the outlet 314 equals the rate of liquid 316 entering the input 312. The liquid continues to be supplied either by bin 336, or recirculated by pump 368 from pool or tank 364, through line 370 to the input 312.

In the absence of rotation of the cylindrical body 310, the liquid 316 exits output 314 at zero position 318, which is located on the plane of zero position as defined earlier. A respective electrooptic cell 398 detects this effect and provides the information to computer 353 through line 395. The computer may record this information, or it may use it to induce a desired action.

If the motor 382, controlled by the computer, or manually, is activated, the cylindrical body 310 is caused to rotate in a direction D at a desired linear speed, and the liquid 316 exits at a discharge position 317, which now is different than the zero position. This is detected by electrooptic cell 397. The distance between the discharge position and the plane of zero position is thus determined. This distance corresponds to an angular viscosity of the liquid at the given values of the operational parameters (Length, Diameter, Rotational Speed, Inclination Angle, and Feeding Rate). The computer 353 may use this information to translate it to angular viscosity as described above, and proceed to appropriate preset actions.

The angular viscosities determined by the methods and apparatus of this invention may be correlated or calibrated with the measurements of other well established and conventional techniques so that the angular viscosity may attain absolute correlation values. This may be done with liquids which are easily adaptable to conventional techniques, and then extrapolated with the teachings of this invention to situations of adverse conditions and hostile environments, such as for example conditions encountered in incinerating kilns.

In a different embodiment, the rotation speed may be varied until the discharge position attains the value of a far position 322, which interrupts the path of a respective electrooptic cell or photocell 392. Then this rotation speed may be correlated with the viscosity value received from conventional methods. One photocell only is required in the practice of this embodiment.

In general, the viscosity may be calibrated or correlated with the viscosity values of conventional methods for each operational parameter used as a variable, and with the rest being kept constant. Of course, combinations of more than one variable operational parameters may be used, with the rest, if any, being kept constant.

The examples in the above description have been given for demonstration purposes only and they should not be construed as limiting the scope of this invention

What is claimed is:

1. An incinerating kiln device capable of controlling the viscosity of molten slag contained within and discharged from the kiln, the device comprising a rotary kiln having a substantially cylindrical shape, an outside skin, a center axis, an inlet, and an outlet opposite the inlet, the kiln being inclined so that the slag exits from the outlet at a discharge position, and wherein the center axis and a line crossing the center axis and having the direction of gravity define a plane of zero position, the distance between the discharge position and the plane of zero position being an indirect measure of the angular viscosity of the slag, the higher said distance the higher the angular viscosity;

first detection means at the outlet of the kiln for detecting the distance between the discharge position and the plane of zero position, thus determining the angular viscosity of the slag; and means for correcting the viscosity of the slag, if the distance between the plane of zero position and the discharge position deviates from a desired value, by feeding an additive to the inlet of the kiln.

2. A device as defined in claim 1, further comprising computer means for processing data received from the distance detection means and thereby control the viscosity correcting means.

3. A device as defined in claim 1, wherein the first detection means comprise a series of heat-resistant rods positioned in a direction substantially parallel to the center axis of the kiln under the outlet of the kiln in a manner that discharged slag falls on at least one of the rods producing a mechanical perturbation on the rod, so that depending on which rod(s) the perturbation occurs, the distance between the discharge position and the plane of zero position is determined.

4. A device as defined in claim 3, wherein the perturbation is detected by a strain gauge mounted at a position of the rod at which the operability of the gauge is not substantially affected by the effects of the kiln and the falling slag.

5. A device as defined in claim 3, wherein the perturbation is detected by electromechanical means.

6. A device as defined in claim 1, wherein the first detection means comprise optical means.

7. A device as defined in claim 6, wherein the optical means comprise a series of photocells positioned under the outlet of the kiln and having a direction of detecting mode substantially parallel to the center axis of the kiln so that depending on which photocell detects falling slag, the distance between the discharge position and the plane of zero position is determined.

8. A device as defined in claim 6, wherein the optical means comprise infra-red means.

9. A device as defined in claim 8, wherein the infrared means comprise an infra-red scanner.

10. A device as defined in claim 9, wherein the infrared means are positioned under the outlet of the kiln and have a direction of scanning mode substantially perpendicular to the center axis of the kiln so that depending on the position of the scan when falling slag is detected, the distance between the discharge position and the plane of zero position is determined.

11. A device as defined in claim 1, wherein the viscosity correcting means comprise bins for containing additives and feeding additives to the kiln.

12. A device as defined in claim 1, further comprising second detection means for detecting and monitoring the temperature of the slag at the outlet of the kiln.

13. A device as defined in claim 1, further comprising third detection mean for detecting and monitoring the temperature of the skin of the kiln.

14. A device as defined in claim 1, further comprising means for lowering the temperature of the slag through the skin of the kiln.

15. A method for controlling the viscosity of a molten slag in an incinerating rotary kiln comprising the steps of:
a) feeding waste into an inlet of the kiln, the kiln being inclined and having a substantially cylindrical shape, a skin, a center axis, and an outlet opposite the inlet, so that the slag exits from the outlet at a discharge position, and
wherein the center axis and a line crossing the center axis and having the direction of gravity define a plane of zero position,
the distance between the discharge position and the plane of zero position being an indirect measure of the angular viscosity of the slag, the higher said distance the higher the angular viscosity;
b) detecting the distance between the discharge position and the plane of zero position, thus determining the angular viscosity of the slag; and
c) correcting the viscosity of the slag, if the distance between the plane of zero position and the discharge position deviates from a desired value, by feeding an additive to the inlet of the kiln.

16. A method as defined in claim 15, further comprising a step of processing in a computer data received from step (b) and applying the processed data for correcting the viscosity in step (c).

17. A method as defined in claim 15, wherein the distance detecting step (b) is performed by means comprising a series of heat-resistant rods positioned in a direction substantially parallel to the center axis of the kiln under the outlet of the kiln in a manner that discharged slag falls on at least one of the rods producing a mechanical perturbation on the rod, so that depending on to which rod(s) the perturbation occurs, the distance between the discharge position and the plane of zero position is determined.

18. A method as defined in claim 17, wherein the perturbation is detected by a strain gauge mounted at a position of the rod at which the operability of the gauge is not substantially affected by the effect of the kiln and the falling slag.

19. A method as defined in claim 17, wherein the perturbation is detected by electromechanical means.

20. A method as defined in claim 15, wherein the distance detecting step (b) involves optical means.

21. A method as defined in claim 6, wherein the optical means comprise a series of photocells positioned under the outlet of the kiln and having a direction of detecting mode substantially parallel to the center axis of the kiln so that depending on which photocell detects falling slag, the distance between the discharge position and the plane of zero position is determined.

22. A method as defined in claim 20, wherein the optical means comprise infra-red means.

23. A method as defined in claim 22, wherein the infra-red means comprise an infra-red scanner.

24. A method as defined in claim 23, wherein the infra-red means are positioned under the outlet of the kiln and have a direction of scanning mode substantially perpendicular to the center axis of the kiln so that depending on position of the scan when falling slag is detected, the distance between the discharge position and the plane of zero position is determined.

25. A method as defined in claim 15, wherein the viscosity correcting step (c) involves bins for containing additives and further comprises a step of feeding additives to the kiln.

26. A method as defined in claim 15, further comprising a step of detecting and monitoring the temperature of the slag at the outlet of the kiln.

27. A method as defined in claim 15, further comprising a step of detecting and monitoring the temperature of the skin of the kiln.

28. A method as defined in claim 1, further comprising a step of lowering the temperature of the slag through the skin of the kiln.

29. A method of determining the angular viscosity of a liquid comprising the steps of:
a) feeding the liquid at a predetermined rate to an inlet of a hollow, inclined, rotating, substantially cylindrical body, the cylindrical body having a center axis, and an outlet opposite the inlet,
so that the liquid exits from the outlet at a discharge position, and
wherein the center axis and a line crossing the center axis and having the direction of gravity define a plane of zero position, the distance between the discharge position and the plane of zero position being an indirect measure of the angular viscosity, the higher said distance the higher the angular viscosity; and
b) detecting the distance between the discharge position and the plane of zero position, thus determining the angular viscosity of the liquid.

30. An apparatus for determining the angular viscosity of a liquid comprising:
a) a hollow, inclined, substantially cylindrical body, the cylindrical body having a center axis, an inlet, and an outlet opposite the inlet;
b) means for rotating the cylindrical body;
c) means for feeding the liquid at a predetermined rate to the inlet of the cylindrical body;
so that the liquid exits from the outlet at a discharge position, and
wherein the center axis and a line crossing the center axis and having the direction of gravity define a plane of zero position,
the distance between the discharge position and the plane of zero position being an indirect measure of the angular viscosity, the higher said distance the higher the angular viscosity; and
c) means at the outlet of the cylindrical body for detecting the distance between the discharge position and the plane of zero position thus determining the angular viscosity of the liquid.

* * * * *